United States Patent [19]

Stemerick et al.

[11] Patent Number: 4,753,965

[45] Date of Patent: Jun. 28, 1988

[54] METHOD OF TREATING MULTIPLE SCLEROSIS WITH CHALCONE DERIVATIVES

[75] Inventors: David M. Stemerick; Sai P. Sunkara; Michael L. Edwards, all of Cincinnati, Ohio

[73] Assignee: Merrell Dow Pharmaceuticals, Inc., Cincinnati, Ohio

[21] Appl. No.: 36,237

[22] Filed: Apr. 9, 1987

[51] Int. Cl.⁴ .......................................... A61K 31/135
[52] U.S. Cl. ..................................................... 514/647
[58] Field of Search ........................................ 514/647

[56] References Cited

U.S. PATENT DOCUMENTS

| | | | |
|---|---|---|---|
| 3,729,313 | 4/1973 | Smith | 96/271 L |
| 3,808,006 | 4/1974 | Smith | 96/88 |
| 4,054,682 | 10/1977 | Kuesters et al. | 427/54 |
| 4,162,162 | 7/1979 | Dueber | 95/115 P |
| 4,279,930 | 7/1982 | Hall et al. | 568/334 |
| 4,290,870 | 9/1981 | Kondoh et al. | 204/159.15 |
| 4,367,280 | 1/1983 | Kondo et al. | 430/281 |

FOREIGN PATENT DOCUMENTS

| | | |
|---|---|---|
| 13960 | 8/1980 | European Pat. Off. . |
| 28305 | 5/1981 | European Pat. Off. . |
| 2558813 | 7/1977 | Fed. Rep. of Germany . |
| 943266 | 12/1963 | United Kingdom . |
| 2081716 | 2/1982 | United Kingdom . |

OTHER PUBLICATIONS

Chem. Abst. 83/170.626 u (1975).
Chemical Abstract 62:14039, V. F. Lavrushin, V. P. Dzyuba and V. N. Tomachev. Zh. Obshch. Chim. 35(1), 95–103 (1965).
Chemical Abstract 60:443, V. F. Lavrushin and V. P. Dzyuba, Zh. Obsch. Khim. 33(8), 2581–2585, (1963).
Chemical Abstract 66:6820, V. F. Lavrushin, V. P. Dzyuba and V. N. Tolmachev. Zh. Obshch. Khim. 36(8), 1374–1380, (1966).

*Primary Examiner*—Stanley J. Friedman
*Attorney, Agent, or Firm*—J. Michael Dixon

[57] ABSTRACT

Certain chalcone derivatives are reported to inhibit the polymerization of tubulin to form microtubules and are therefore antimitotic agents which can be used to control the growth of tumor tissue and can be used as antigout agents.

14 Claims, No Drawings

METHOD OF TREATING MULTIPLE SCLEROSIS WITH CHALCONE DERIVATIVES

FIELD OF THE INVENTION

This invention relates to certain chalcone derivatives which inhibit the destruction of the myelin sheath covering the axons of the central nervous system and are thus useful in the treatment of multiple sclerosis.

BACKGROUND OF THE INVENTION

Cell division in eukaryotic cells is divided into two sequential phases, mitosis followed by cytokinesis. At the onset of mitosis, cytoplasmic microtubules disassemble into tubulin molecules which are then polymerized to form the mitotic spindle. The mitotic spindle, an element of the mitotic apparatus, ensures that replicated chromosomes are precisely divided between the two daughter cells at division. The polymerization of tubuline to form the mitotic spindle is highly sensitive to chemical agents which bind tubulin. Colchicine, for example, has long been known to inhibit the polymerization of tubulin. When administered to a dividing cell, colchicine causes the mitotic spindle to disappear and blocks mitosis. Anticancer drugs such as vinblastine and vincristine induce the formation of paracrystalline aggregates of tubulin and thus deplete the supply of tubulin available for the formation of the mitotic spindle. Absence of the spindle, of course, interrupts mitosis and prevents cell division. Cells thus blocked from division ultimately die.

Applicants have now discovered a new class of antimitotic agents which prevent spindle formation by causing tubulin aggregation as do vinblastine and vincristine. These new antimitotic agents are, however, much less toxic than are other antimitotic agent.

Myelin is a fatty coating surrounding the axons of the nervous system and serves to insulate the electrical signals in the axons. By insulating the axons, nerve impulses are transmitted more rapidly and efficiently. In the peripheral nervous system, myelin is produced by and is a part of the cell surface of Schwann cells, a set of cells which lie parallel to the axons. The myelin of each Schwann cell is used to surround a single axon. In the central nervous system, the insulating myelin sheaths are produced by the oligodendroglial cells. Unlike the Schwann cells, the myelin of an oligodendroglial cell may surround many axons.

Multiple sclerosis is a demyelinating disease in which the myelin sheaths of the central nervous system are destroyed. Once destroyed, the axons are left exposed and are unable to effectively transmit nerve impulses. Symptoms include loss of visual acuity, muscular weakness, and spasticity. Typically the victim of multiple sclerosis will experience periods where the symptoms are exacerbated followed by periods where the symptoms nearly vanish. The course of the disease is normally progressive and recovery between periods of exacerbation is diminished, the length of time between periods of exacerbations is reduced, and the length of each period of exacerbation increases. The cause of multiple sclerosis is unknown but the most recent evidence increasingly supports the notion of a viral agent or autoimmunological source. Indeed the lesions of multiple sclerosis are mimicked by the lesions of experimental allergic encephalomyelitis, an experimentally induced autoimmunological disorder in which the myelin sheaths of the central nervous system are destroyed. This immunological connection has prompted the use of various immunosuppressive agents such as azathioprine, cyclophosphamide, and cyclosporin A to treat multiple sclerosis. Applicants have now discovered that certain chalcone derivatives inhibit the destruction of the myelin sheath in the central nervous system as evidenced by the inhibition of paralysis of hind limbs in test animals and are thus useful in the treatment of multiple sclerosis.

SUMMARY OF THE INVENTION

This invention relates to the use of certain chalcone derivatives of structure 1:

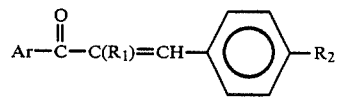

wherein
Ar is a 2,5-dimethoxyphenyl, 2,3,4-trimethoxyphenyl, or 3,4,5-trimethoxyphenyl group;
$R_1$ is a hydrogen, $(C_1-C_4)$alkyl, chloro, or bromo group; and
$R_2$ is a $-N(R)_2$ or $-NHCOR$ wherein R is a $(C_1-C_4)$alkyl group
and the pharmaceutically acceptable salts thereof to inhibit the destruction of the myelin sheath in the central nervous system and are useful in the treatment of multiple sclerosis.

DETAILED DESCRIPTION OF THE INVENTION

The term "$(C_1-C_4)$alkyl" as used herein means a straight or branched alkyl group of from 1 to 4 carbon atoms, including methyl, ethyl, n-propyl, isopropyl, n-butyl, isobutyl, t-butyl, and sec-butyl.

The compounds of this invention contain a carbon-carbon double bond and thus geometric isomerism is possible. The benzoyl group (ArC(O)) of the structure 1 compounds can be either cis or trans to the phenyl group (p-$(R_2)C_6H_4$). Both such cis and trans compounds are intended to be included within the scope of this invention. In naming the compounds of structure 1, the prefixes "(E)" and "(Z)" are used in the conventional manner to indicate stereochemistry at the carbon-carbon double bond. If no stereochemical designation is given, both the substantially pure isomers and mixtures are intended. Those compounds of structure 1 wherein the benzoyl group is trans to the phenyl group are preferred.

As is the case for most groups of therapeutically effective compounds, certain subclasses of the compounds are more effective than others. In this instance those compounds wherein $R_1$ is a $(C_1-C_4)$alkyl, those compounds wherein Ar is 2,5-dimethoxyphenyl, and those compounds wherein $R_2$ is a $-N(R)_2$ group are preferred. Those compounds wherein $R_2$ is a dimethylamino group are more preferred. Those compounds wherein $R_1$ is a methyl group are also more preferred. The compounds wherein the benzoyl group is trans to the phenyl group are also preferred to those wherein the benzoyl group is cis to the phenyl group. The most preferred compound of structure 1 is the compound wherein $R_1$ is a methyl group, $R_2$ is a dimethylamino group, and Ar is a 2,5-dimethoxyphenyl group, that is the compound 1-(2,5-dimethoxyphenyl)-3-[4-(dimethylamino)phenyl]-2-methyl-2-propen-1-one or α-methyl-4-dimethylamino-2',5'-dimethoxychalcone.

The compounds of structure 1 inhibit the polymerization of tubulin, and thus the formation of microtubules, that ubiquitous substance of eukaryotic cells which serves a variety of functions, most importantly, to separate the duplicated sets of chromosomes during cell mitosis. The ability of the compounds of structure 1 to inhibit mitosis can be illustrated by their ability to cause mitotic accumulation, i.e., increase the number of cells in a cell culture undergoing mitosis, and by their ability to inhibit the growth of HeLa cells.

Effect of
α-methyl-4-dimethylamino-2',5'-dimethoxychalcone and Vinblastine of the Mitotic Accumulation and Growth of HeLa Cells

| COMPOUND | MITOTIC ARREST Minimum Effectice Concentration (ʋg/ml) | | GROWTH INHIBITION IC$_{50}$ (ʋg/ml) |
|---|---|---|---|
| | 6 hours | 1 hour | |
| COMPOUND | 0.0038 | 0.06 | 0.015 |
| VINBLASTINE | 0.0015 | 0.015 | 0.015 |

Exponentially growing human carcinoma (HeLa) cells are plated at a density of $1 \times 10^4$ cells/well in a 24 well plate. The compounds were dissolved in dimethylsulfoxide and diluted with complete medium. The cells were inoculated with the medium containing the test compound either for 6 hours or 1 hour. For the 1 hour test, the cells were washed twice and further grown for 18 hours in the presence of drug free medium. The mitotic cells in the supernatent were collected and were pooled with the trypsinized cells and cytopreps were made on slides using a cytocentrifuge. The slides were fixed with Carnoy's solution, stained with acetoorcein, and the mitotic index was determined. For growth inhibition studies, exponentially growing HeLa cells were incubated at a density of $1 \times 10^5$ cells/35 mm dish with a number of dilutions of the test compound in the medium. The plates were incubated at 37° C. in a CO$_2$ incubation. At the end of 72 hours the cells were collected by trypinization and counted and the IC$_{50}$ (ʋg/ml) was determined.

Because of the ability of the compounds of structure 1 to inhibit the formation of microtubules, the compounds are antimitotic agents, substances which prevent cell mitosis. Like other antimitotic agents such as colchicine, vinblastine, and vincristine the compounds of structure 1 are useful in the treatment of gout.

Gout is an arthritic condition in which crystals of monosodium urate deposit in the peripheral joints. The presence of these crystals causes inflammation of the joint and pain. The crystal deposition is made possible by the presence of hyperuricemic fluids, however, not all hyperuricemic individuals experience gout. Therapy involves use of anti-inflammatory drugs and colchicine as well as the concomitant lowering of serum urate concentration. While colchicine is highly effective in controlling an acute attack of gout, the drug is highly toxic and its use in long term therapy is undesirable. The mechanism by which colchicine treats gout is poorly understood, but is presumably a function of the antimitotic or tubulin polymerization inhibition activity of colchicine. The compounds of structure 1 by virtue of their antimitotic activity and their ability to prevent tubulin polymerization are also antigout agents.

The compounds of structure 1 inhibit the destruction of myelin sheath surrounding the axons of the central nervous system. This myelin destruction is characteristic in those individuals suffering from multiple sclerosis. By preventing the destruction of myelin in multiple sclerosis patients, the compounds of structure 1 will prevent or reduce the progressive nature of the disease, prevent or increase the length of time between the recurrent episodes of the disease, and prevent or suppress the formation of the scarlike, multiple sclerotic plaques characteristic of the disease. The ability of the compounds of this invention to inhibit the destruction of myelin and to treat patients suffering from multiple sclerosis can be demonstrated by their ability to affect the symptoms of experimental allergic encephalomyelitis (EAE), a condition brought about by the immunization of an individual with myelin. This myelin brings about an immune response in the individual in which the myelin sheath is destroyed. EAE is an experimental model of multiple sclerosis.

Effect of
α-methyl-4-dimethylamino-2',5'-dimethoxychalcone on Experimental Allergic Encephalomyelitis (EAE) in Rats

| TREATMENT | DOSE (mg/kg) | PERCENT INCIDENCE OF PARALYSIS | PARALYSIS TIME (Days) (Mean ± S.E.) |
|---|---|---|---|
| CONTROL | — | 90(7/19)[a] | 9.3 ± 0.27 |
| COMPOUND | 6.25 | 90(9/10) | 9.7 ± 0.36 |
| COMPOUND | 12.5 | 80(8/10) | 9.4 ± 0.26 |
| COMPOUND | 25.0 | 40(7/18) | 10.8 ± 0.54[b] |
| HYDROCORTISONE | 25.0 | 74(14/19) | 11.0 ± 0.28[b] |

EAE was induced in rats as described by Rosenthal and Nagra, Proc. Soc. Exp. Biol. Med. 125, 149 (1967). Lewis strain rats ranging in weight from 100-200 g were sensitized with encephalitogenic emulsion consisting of homogenized spinal cord in complete Freund's adjuvant. The test compound and hydrocortisone (HC) were administered in polyvinylpyrrolidone vehicle. The test compound was administered i.p. once daily from day 1 through day 10. HC was administered s.c. once every other day from day 1 through day 10. The incidence of paralysis was recorded and mean paralysis time was calculated.
[a](number paralyzed/total number of animals.
[b]Significant at $p < 0.01$.

As used herein the term patient is taken to mean warm blooded animals such as mammals, for example, dogs, rats, mice, cats, guinea pigs, horses, cattle, sheep, and primates including humans.

The therapeutically effective amount of the active ingredient to be administered can vary widely according to the particular dosage unit employed, the period of treatment, the age and sex of the patient treated and the nature and extent of the disorder treated. The total amount of the active ingredient to be administered will generally range from about 1 mg/kg to 100 mg/kg and preferably from 3 mg/kg to 25 mg/kg. A unit dosage may contain from 25 to 500 mg of active ingredient, and can be taken one or more times per day. The active compound of formula 1 can be administered with a pharmaceutical carrier using conventional dosage unit forms either orally, parenterally, or topically.

The preferred route of administration is oral administration. For oral administration the compounds can be formulated into solid or liquid preparations such as capsules, pills, tablets, troches, lozenges, melts, powders, solutions, suspensions, or emulsions. The solid unit dosage form can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combinations with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptable surfactant, suspending agent, or emulsifying agent.

The compounds of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically acceptable adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures. The parenteral compositions of this invention will typically contain from about 0.5 to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The active ingredient may also be administered by means of a sustained release system whereby the compound of formula 1 is gradually released at a controlled, uniform rate from an inert or bioerodible carrier by means of diffusion, osmosis, or disintegration of the carrier during the treatment period. Controlled release drug delivery systems may be in the form of a patch or bandage applied to the skin or to the buccal, sublingual, or intranasal membranes, an ocular insert placed in the cul de sac of the eye, or a gradually eroding tablet or capsule or a gastrointestinal reservoir administered orally. Administration by means of such sustained release delivery systems permits the tissues of the body to be exposed constantly for a prolonged time period to a therapeutically or prophylactically effective dosage of a compound of formula 1. The unit dosage of the compound administered by means of a sustained release system will approximate the amount of an effective daily dosage multiplied by the maximum number of days during which the carrier is to remain on or in the body of the host. The sustained release carrier may be in the form of a solid or porous matrix or reservoir and may be formed from one or more natural or synthetic polymers, including modified or unmodified cellulose, starch, gelatin, collagen, rubber, polyolefins, polyamides, polyacrylates, polyalcohols, polyethers, polyesters, polyurethanes, polysulphones, polysiloxanes, and polyimides as well as mixtures and copolymers of these polymers. The compounds of formula 1 may be incorporated in the sustained release carrier in a pure form or may be dissolved in any suitable liquid or solid vehicle, including the polymer of which the sustained release carrier is formed.

The compounds of this invention are useful both in the free base form and in the form of acid addition salts. The acid addition salts are simply a more convenient form for use and, in practice, use of the salt amounts to use of the free base. The expression "pharmaceutically acceptable acid addition salts" is intended to apply to any non-toxic organic or inorganic acid addition salts of the base compounds of formula 1. Illustrative inorganic acids which form suitable salts include hydrochloric, hydrobromic, sulfuric, and phosphoric acids and acid metal salts such as sodium monohydrogen orthophosphate and potassium hydrogen sulfate. Illustrative organic acids which form suitable salts include the mono, di, and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, and 2-phenoxybenzoic acids. Other organic acids which form suitable salts are the sulfonic acids such as methane sulfonic acid and 2-hydroxyethane sulfonic acid. Either the mono- or the di-acid salts can be formed, and such salts can exist in either a hydrated or a substantially anhydrous form. The acid salts are prepared by standard techniques such as by dissolving the free base in aqueous or aqueous-alcohol solution or other suitable solvent containing the appropriate acid and isolating by evaporating the solution, or by reacting the free base in an organic solvent in which case the salt separates directly or can be obtained by concentration of the solution. In general the acid addition salts of the compounds of this invention are crystalline materials which are soluble in water and various hydrophilic organic solvents and which in comparison to their free base forms, demonstrate higher melting points and an increased solubility.

Applicants have prepared the chalcones of stucture 1 wherein $R_1$ is hydrogen by the base catalyzed condensation of an acetophenone derivative of structure 2 with a benzaldehyde derivative of structure 3 as illustrated in scheme I

SCHEME I

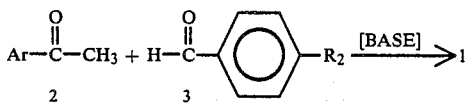

wherein Ar and $R_2$ are as defined above for structure 1. Any base useful in aldol condensation reactions can be used, for example, an alkali metal hydroxide or carbonate such as sodium hydroxide, sodium carbonate, potassium hydroxide, potassium carbonate, or sodium hydrogen carbonate. Sodium hydroxide is the preferred base catalyst. Typically about 0.01 to about 1 molar equivalent of the base catalyst will be used and the structure 2 acetophenone and the structure 3 benzaldehyde will be present in equimolar amounts although a slight molar excess of one reactant or the other may be advantageous in some circumstances. The use of a solvent will facilitate the reaction and isolation of the product. Any solvent which does not interfere with the aldol condensation can be used. Suitable solvents include the etheral solvents such as diethyl ether, tetrahydrofuran (THF), or p-dioxan; a chlorinated hydrocarbon such as chloroform, methylene chloride, or carbon tetrachloride; alcoholic solvents such as methanol or ethanol; aromatic solvents such as benzene and toluene; or the hydrocarbon solvents such as hexane or petroleum ethers. Ethanol is the preferred solvent. The reactants are mixed and allowed to react for from about 6 hours to about 5 or 6 days depending on the reactants, the base, amount of base, and the temperature which can be from about 0° C. to about 60° C., and will conveniently be room temperature, 25° C. The product can be isolated from the reaction mixture by, for example, simple filtration if the product crystallizes from the reaction mixture or by solvent removal and recrystallization from methanol in the case of an oil or distillation in the case of a liquid.

The compounds of structure 1 wherein $R_1$ is a chloro group are prepared by the reaction of sulfuryl chloride ($SO_2Cl_2$) with the corresponding compound of structure 1 wherein $R_1$ is a hydrogen group. This reaction is performed by adding sulfuryl chloride, preferably in solution, to a solution of the chalcone derivative of structure 1 wherein $R_1$ is hydrogen group. Preferably the addition of sulfuryl chloride will take about 10 to 30 minutes to minimize the temperature build up of this very exothermic reaction. Approximately equimolar amounts of the structure 1 compound wherein $R_1$ is a hydrogen group and sulfuryl chloride can be used, however, a small excess, e.g. 10%, of sulfuryl chloride is preferred. The reaction will take about 30 minutes to about 5 hours, typically about 1 hour depending on the solvent, the reactant, and the temperature which can be from about $-30°$ C. to about $25°$ C. Conveniently the temperature of the reaction mixture during and subsequent to the addition of sulfuryl chloride can be maintained at about 0° C. with an ice bath. The product can be isolated from the reaction mixture by treatment with a base such as sodium carbonate solution followed by flash chromatography on silica gel. The product can then be purified by any art known procedure such as by recrystallization from ethyl acetate. Suitable solvents include the etheral solvents such as diethyl ether, tetrahydrofuran (THF), or p-dioxan; a chlorinated hydrocarbon such as chloroform, methylene chloride, or carbon tetrachloride; aromatic solvents such as benzene and toluene; or the hydrocarbon solvents such as hexane or petroleum ethers. Preferably the solvent will be methylene chloride or more preferably a mixture of methylene chloride and hexane.

The compounds of structure 1 wherein $R_1$ is a bromo group are prepared by the reaction of molecular bromine with the corresponding compound of structure 1 wherein $R_1$ is a hydrogen group. This reaction is performed by adding one equivalent of molecular bromine, preferably dropwise and preferably as a solution, to a one equivalent solution of the chalcone starting material. After about 30 minutes to about 2 hours, typically about 30 to 45 minutes, the reaction mixture is washed with an aqueous solution of a base such as sodium hydroxide (1N) or sodium carbonate (saturated) after which the solvent is removed by evaporation. The product can be purified in any suitable way such as by chromatography and/or recrystallization using a mixture of ethyl acetate and hexane.

The compounds of structure 1 where $R_1$ is an alkyl group are prepared by the base catalyzed condensation of an acetophenone derivative of structure 4 with a benzaldehyde derivative of structure 5 as illustrated in scheme II.

SCHEME II

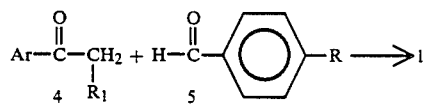

While any base catalyst may be used, piperidine acetate is preferred. The piperidine acetate catalyst is formed in the reaction vessel by simply mixing piperidine and acetic acid. While any quantity of the catalyst is useful, preferably about 1 or 2 molar equivalents of the catalyst will be employed. The use of a dehydrating agent such as 3A molecular sieves also facilitates the reaction. The use of a solvent is also advantageous and any suitable solvent mentioned above can be used, preferably ethanol. Typically an equimolar quantity of the structure 4 acetophenone and the structure 5 benzaldehyde will be used, however it may be advantageous to use an excess of one reagent or the other in certain instances. The reaction is allowed to proceed until substantially complete as indicated by, for example, thin-layer, silica gel chromatography. The time of the reaction will depend on various factors such as the reactants, the acid catalyst, and the temperature which can be from about 0° C. to about 120° C., and conveniently can be the reflux temperature of the reaction mixture.

EXAMPLES

The following examples are intended to illustrate the preparation of the compounds of this invention and the pharmaceutical compositions of these compounds.

Example 1

PREPARATION OF
α-METHYL-4-DIMETHYLAMINO-2',5'-DIMETHOXYCHALCONE

A mixture of 2,5-dimethoxypropiophenone (1.8 g, 0.009 mole), piperidine (1.8 ml), 4-dimethylaminobenzaldehyde (1.38 g, 0.009 mole), ethanol (15 ml), and acetic acid (0.9 ml) was heated at its reflux temperature. The condensate was made to pass through a bed of 12 g, 3A molecular sieves and refluxing was continued until the reaction was complete as indicated by a thin layer chromatography (25% ethyl acetate/hexane). The solvent was then removed at reduced pressure and the resulting dark solid was chromatographed on a silica gel column eluting with a mixture of ethyl acetate and hexane. Recrystallization from diethyl ether/hexane yielded the title compound, m.p. 79°–80° C. Elemental analysis for $C_{20}H_{23}NO_3$: Calcd: C, 73.82; H, 7.12; N, 4.31%. Found: C, 73.78; H, 7.25; N, 4.222%.

Also prepared by substantially the same procedure as in example 1 were:

α-methyl-4-diethylamino-2',5'-dimethoxychalcone, m.p. 60°–61° C.; Elemental analysis for $C_{22}H_{27}NO_3$: Calcd: C, 74.75; H, 7.70; N, 3.96%; Found: C, 74.78 (74.76); H, 7.74 (7.75); N, 3.94% (3.68%);

α-methyl-4-dimethylamino-2',3',4'-trimethoxychalcone, m.p. 96°–97° C.; Elemental analysis for $C_{21}H_{25}NO_4$: Calcd: C, 70.96; H, 7.09; N, 3.94%; Found: C, 70.73; H, 7.09; N, 3.74%;

α-methyl-4-dimethylamino-3',4',5'-trimethoxychalcone, m.p. 113°–114° C.;

α-ethyl-4-dimethylamino-2',3',4'-trimethoxychalcone, b.p. 260° C., 0.8 mm Hg; Elemental analysis for $C_{22}H_{27}NO_4$: Calcd: C, 72.03; H, 7.62; N, 3.65%; Found: C, 72.08; H, 7.70; N, 3.43%;

α-methyl-4-diethylamino-2',3',4'-trimethoxychalcone, m.p. 78°–79° C.; Elemental analysis for $C_{23}H_{29}NO_4$: Calcd: C, 72.03; H, 7.62; N, 3.65%; Found: C, 72.08; H, 7.70; N, 3.43%; and α-methyl-4-diethylamino-3',4',5'-trimethoxychalcone, b.p. 220°–225° C., 0.6 mm Hg; Elemental analysis for $C_{23}H_{29}NO_4$: Calcd: C, 72.03; H, 7.62; N, 3.65%; Found: C, 71.74 (71.66); H, 7.58 (7.63); N, 3.44% (3.53%).

Example 2

PREPARATION OF
4-DIMETHYLAMINO-2',3',4'-TRIMETHOXYCHALCONE

Sodium hydroxide (0.5 ml of 2N) was added to a mixture of trimethoxyacetophenone (2.1 g, 0.01 mole), dimethylaminobenzaldehyde (1.49 g, 0.01 mole), and ethanol (50 ml). The reaction mixture was allowed to stir at room temperature until a thin layer chromatography (50% ethyl acetate in hexane) indicated that the reaction was complete. After cooling to about 0° C., the mixture was filtered, the solid residue washed with water, then with methanol. Recrystallization from methanol gave the title compound, m.p. 145°–146° C. Elemental analysis for $C_{20}H_{23}NO_4$: Calcd: C, 70.36; H, 6.79; N, 4.10%. Found: C, 70.21; H, 6.98; N, 3.83%.

Also prepared by substantially the same procedure as in example 2 were:

4-dimethylamino-2',3',4'-trimethoxychalcone, m.p. 88°–89° C.; Elemental analysis for $C_{20}H_{23}NO_4$: Calcd: C, 70.36; H, 6.29; N, 4.10%; Found: C, 70.18; H, 6.98; N, 4.23%;

4-acetamido-2',3',4'-trimethoxychalcone, m.p. 113°–114° C.; Elemental analysis for $C_{20}H_{21}NO_5$: Calcd: C, 67.59; H, 5.96; N, 3.94%; Found: C, 67.26 (67.17); H, 5.90 (5.99); N, 3.78% (3.82%);

4-acetamido-3',4',5'-trimethoxychalcone, m.p. 190°–191° C.; Elemental analysis for $C_{20}H_{21}NO_5$: Calcd: C, 67.59; H, 5.96; N, 3.94%; Found: C, 67.06 (67.22, 67.80); H, 6.03 (6.23, 5.95); N, 3.91% (3.90%, 3.95%); and 4-acetamido-2',5'-dimethoxychalcone, m.p. 154°–155° C.; Elemental analysis for $C_{19}H_{19}NO_4$: Calcd: C, 70.14; H, 5.89; N, 4.31%; Found: C, 69.54 (69.46); H, 5.95 (5.98); N, 4.10% (4.30%).

Example 3

PREPARATION OF
α-CHLORO-4-DIMETHYLAMINO-3',4',5'-TRIMETHOXYCHALCONE

A solution of sulfuryl chloride (0.44 ml, 0.0055 mole) in carbon tetrachloride (2 ml) was added over about 20 minutes to a stirred solution of 4-dimethylamino-3',4',5'-trimethoxychalcone (1.7 g, 0.0055 mole) in carbon tetrachloride (20 ml) and methylene chloride (4 ml), cooled in an ice bath to about 0° C. After about 1 hour, carbon tetrachloride (100 ml) was added and the mixture was washed with a saturated, aqueous solution of sodium carbonate, then dried with magnesium sulfate. Chromatography on a silica gel column eluting with 25% ethyl acetate/hexane followed by recrystallization from ethanol gave the title compound, m.p. 86°–87° C. Elemental analysis for $C_{20}H_{22}ClNO_4$: Calcd: C, 63.91; H, 5.90; N, 3.73; Cl, 9.43%; Found: C, 64.05; H, 5.96; N, 3.63; Cl, 9.32%. Also prepared by substantially the same procedure as in example 3 were:

α-chloro-4-dimethylamino-2',3',4'-trimethoxychalcone, m.p. 125°–126° C.; Elemental analysis for $C_{20}H_{22}ClNO_4$: Calcd: C, 63.91; H, 5.90; N, 3.73; Cl, 9.43%; Found: C, 64.15; H, 6.00; N, 3.65; Cl, 9.32%; and α-chloro-4-dimethylamino-2',5'-dimethoxychalcone, b.p. 205°–210° C., 0.1 mm Hg.

Example 4

PREPARATION OF α-BROMO-4-DIMETHYLAMINO-2',3',4'-TRIMETHOXYCHALCONE

A solution of bromine (2,44 g, 0.0152 mole) in carbon tetrachloride (20 ml) was added dropwise to a solution of 4-dimethylamino-3',4',5'-trimethoxychalcone (5.2 g, 0.0152 mole) in carbon tetrachloride (150 ml). After stirring for about 20 minutes, the solvent was removed at reduced pressure. The residue was dissolved in ethyl acetate and the resulting solution washed with a saturated solution of sodium carbonate for about 3 minutes. The organic phase was washed with a saturated, aqueous solution of sodium chloride, then dried with magnesium sulfate. After removing the solvent at reduced pressure, the residue was chromatographed on a silica gel column eluting with a mixture of ethyl acetate and hexane, then recrystallized from ethyl acetate/hexane to give the title compound, m.p. 139°–140° C.

α-Bromo-4-dimethylamino-2',5'dimethoxychalcone, m.p. 74°–75° C. (Elemental analysis for $C_{19}H_{20}BrNO_3$: Calcd: C, 59.71, H, 5.01, N, 3.48, Br, 19.87%; Found: C, 59.58 (58.62), H, 5.21 (5.29), N, 3.53 (3.62), Br, 20.20%) was prepared by substantially the same procedure as in example 4.

Example 5

PREPARATION OF A TABLET FORMULATION

Tablets can be prepared each having the following composition.

| INGREDIENT | QUANTITY (mg) |
| --- | --- |
| α-methyl-4-dimethylamino-2',3',4'-trimethoxychalcone | 100 |
| Cornstarch | 15 |
| Lactose | 33.5 |
| Magnesium Stearate | 1.5 |

Example 6

PREPARATION OF A CAPSULE FORMULATION

Capsules can be prepared each having the following composition.

| INGREDIENT | QUANTITY (mg) |
| --- | --- |
| α-methyl-4-diethylamino-3',4',5'-trimethoxychalcone | 400 |
| Talc | 40 |
| Sodium Carboxymethylcellulose | 40 |
| Starch | 120 |

Example 7

PREPARATION OF A PARENTERAL FORMULATION

A parenteral formulation is prepared each unit dosage having the following composition.

| INGREDIENT | QUANTITY |
| --- | --- |
| 4-dimethylamino-2',5'-dimethoxychalcone | 1.0 g |
| Polyoxyethylene Sorbitan Monooleate | 2.0 g |
| Sodium Chloride | 0.128 g |
| Water for Injection qs ad | 20.0 ml |

We claim:

1. A method for inhibiting destruction of the myelin sheath covering an axon in the central nervous system of a patient suffering from multiple sclerosis which comprises administering to said patient suffering from said multiple sclerosis an effective amount of chalcone derivative of the structure

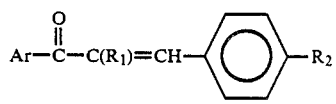

wherein
Ar is a 2,5-dimethoxyphenyl, 2,3,4-trimethoxyphenyl, or 3,4,5-trimethoxyphenyl group;
$R_1$ is a hydrogen, $(C_1-C_4)$alkyl, chloro, or bromo group; and
$R_2$ is a $-N(R)_2$ or $-NH(O)R$ wherein R is a $(C_1-C_4)$alkyl group, or a pharmaceutically acceptable salt thereof.

2. A method of claim 1 wherein $R_1$ is a $(C_1-C_4)$ group.

3. A method of claim 1 wherein $R_1$ is a methyl group.

4. A method of claim 1, 2, or 3 wherein $R_2$ is a $-N(R)_2$.

5. A method of claim 4 wherein R is a methyl group.

6. A method of any of the preceding claims wherein Ar is a 2,5-dimethoxyphenyl group.

7. A method of claim 1 wherein $R_1$ is a methyl group, $R_2$ is a dimethylamino group, and Ar is a 2,5-dimethoxyphenyl group.

8. A method of treating a human suffering from multiple sclerosis which comprises administering to said human suffering from multiple sclerosis an effective amount of a chalcone derivative of the structure

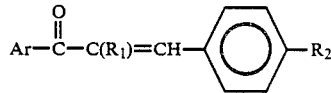

wherein
Ar is a 2,5-dimethoxyphenyl, 2,3,4-trimethoxyphenyl, or 3,4,5-trimethoxyphenyl group;
$R_1$ is a hydrogen, $(C_1-C_4)$alkyl, chloro, or bromo group; and
$R_2$ is a $-N(R)_2$ or $-NH(O)R$ wherein R is a $(C_1-C_4)$alkyl group, or a pharmaceutically acceptable salt thereof.

9. A method of claim 8 wherein $R_1$ is a $(C_1-C_4)$ group.

10. A method of claim 8 wherein $R_1$ is a methyl group.

11. A method of claim 8, 9, or 10 wherein $R_2$ is a $-N(R)_2$.

12. A method of claim 11 wherein R is a methyl group.

13. A method of any of the preceding claims wherein Ar is a 2,5-dimethoxyphenyl group.

14. A method of claim 8 wherein $R_1$ is a methyl group, $R_2$ is a dimethylamino group, and Ar is a 2,5-dimethoxyphenyl group.